(12) United States Patent
Yamamoto

(10) Patent No.: US 9,156,648 B2
(45) Date of Patent: Oct. 13, 2015

(54) ELASTIC THREAD SUPPLY DEVICE

(75) Inventor: Hiroki Yamamoto, Kagawa (JP)

(73) Assignee: UNICHARM CORPORATION, Ehime (JP)

( * ) Notice: Subject to any disclaimer, the term of this patent is extended or adjusted under 35 U.S.C. 154(b) by 573 days.

(21) Appl. No.: 13/519,376

(22) PCT Filed: Dec. 27, 2010

(86) PCT No.: PCT/JP2010/073582
§ 371 (c)(1),
(2), (4) Date: Oct. 4, 2012

(87) PCT Pub. No.: WO2011/081140
PCT Pub. Date: Jul. 7, 2011

(65) Prior Publication Data
US 2013/0032656 A1 Feb. 7, 2013

(30) Foreign Application Priority Data
Dec. 28, 2009 (JP) ................. 2009-298639

(51) Int. Cl.
*B65H 59/38* (2006.01)
*B65H 51/30* (2006.01)
*A61F 13/15* (2006.01)
*D02H 1/00* (2006.01)

(52) U.S. Cl.
CPC .......... *B65H 51/30* (2013.01); *A61F 13/15593* (2013.01); *A61F 13/15772* (2013.01); *B65H 59/388* (2013.01); *D02H 1/00* (2013.01); *B65H 2701/31* (2013.01); *B65H 2701/319* (2013.01)

(58) Field of Classification Search
CPC .... B65H 59/388; B65H 59/387; B65H 59/06; B65H 2701/319
USPC ........ 242/412, 412.1, 420, 420.6, 421.4, 563, 242/564, 151
See application file for complete search history.

(56) References Cited

U.S. PATENT DOCUMENTS

| 4,081,301 A | 3/1978 | Buell |
| 4,666,542 A | 5/1987 | De Jonckheere |
| 4,917,696 A | 4/1990 | De Jonckheere |
| 5,779,689 A | 7/1998 | Pfeifer et al. |
| 6,079,656 A * | 6/2000 | Schmodde et al. ........ 242/365.7 |

(Continued)

FOREIGN PATENT DOCUMENTS

| CN | 1276196 A | 12/2000 |
| CN | 1446172 A | 10/2003 |

(Continued)

OTHER PUBLICATIONS

Extended European Search Report dated Aug. 30, 2013, corresponds to European patent application No. 10840996.2.

(Continued)

*Primary Examiner* — William E Dondero
(74) *Attorney, Agent, or Firm* — Hauptman Ham, LLP

(57) ABSTRACT

An elastic thread supply device including a tension controller configured to control the stress acting upon an elastic thread drawn from an elastic thread package, and a drive roll configured to supply the elastic thread dispensed from the tension controller to a processing line. The drive roll operates at a supply velocity slower than a conveyance velocity of a web, and increases or decreases the supply velocity depending on the fluctuation in the conveyance velocity.

11 Claims, 6 Drawing Sheets

(56) References Cited

U.S. PATENT DOCUMENTS

| | | |
|---|---|---|
| 8,512,304 B2 | 8/2013 | Baba et al. |
| 2007/0138331 A1* | 6/2007 | Bett et al. ................. 242/418.1 |
| 2007/0152093 A1 | 7/2007 | Hartzheim |
| 2008/0210804 A1* | 9/2008 | Barea ............................ 242/416 |
| 2008/0283653 A1* | 11/2008 | Bing-Wo et al. ............. 242/410 |

FOREIGN PATENT DOCUMENTS

| | | |
|---|---|---|
| EP | 115286 A1 | 8/1984 |
| JP | 5726219 B2 | 6/1982 |
| JP | 57133201 A | 8/1982 |
| JP | 59112008 A | 6/1984 |
| JP | 63126903 A | 5/1988 |
| JP | 8132576 A | 5/1996 |
| JP | 8296155 A | 11/1996 |
| JP | 9564 A | 1/1997 |
| JP | 10121342 A | 5/1998 |
| JP | 10259535 A | 9/1998 |
| JP | 11500499 A | 1/1999 |
| JP | 11314840 A | 11/1999 |
| JP | 2999886 B2 | 1/2000 |
| JP | 2000160460 A | 6/2000 |
| JP | 3086141 B2 | 9/2000 |
| JP | 2001039627 A | 2/2001 |
| JP | 2002102277 A | 4/2002 |
| JP | 3506572 B2 | 3/2004 |
| JP | 2004-521842 A | 7/2004 |
| JP | 200522810 A | 1/2005 |
| JP | 200567791 A | 3/2005 |
| JP | 2005067791 A | 3/2005 |
| JP | 2010526000 A | 7/2010 |
| WO | 2008078610 A1 | 7/2008 |
| WO | 2008131252 A1 | 10/2008 |

OTHER PUBLICATIONS

"37922 Strand Control", Research Disclosure, Mason Publications, Hampshire, GB, No. 379, Nov. 1, 1995, p. 729/730, XP000549189.

Information Submission mailed May 7, 2014, corresponds to Japanese patent application No. 2009-298639.

Information Submission mailed May 20, 2014, corresponds to Japanese patent application No. 2009-298639.

Office Action mailed Aug. 26, 2014, corresponds to Japanese patent application No. 2009-298639.

Information Submission received on Jun. 13, 2013 corresponds to Japanese patent application No. 2009-298639.

Information Submission received on Jun. 19, 2013 corresponds to Japanese patent application No. 2009-298639.

Office Action mailed Aug. 6, 2013 corresponds to Chinese Patent Application No. 201080059642.9.

International Search Report and Written Opinion for PCT/JP2010/073582, dated Apr. 5, 2011.

Office Action issued Apr. 8, 2014, corresponds to Chinese patent application No. 201080059642.9.

Office Action mailed Jan. 7, 2014, corresponds to Japanese patent application No. 2009-298639.

Office Action mailed Jun. 2, 2015, corresponding to Japanese patent application No. 2009-298639.

* cited by examiner

ELASTIC THREAD SUPPLY DEVICE

RELATED APPLICATIONS

The present application is a National Phase of International Application Number PCT/JP2010/073582, filed Dec. 27, 2010, and claims priority from Japanese Application Number 2009-298639, filed Dec. 28, 2009.

TECHNICAL FIELD

The present invention relates to an elastic thread supply device, by which an elastic thread is supplied to a processing line through overend unwinding for sequential drawing of the elastic thread in an axial core direction of an elastic thread package around which the elastic thread is wound.

BACKGROUND ART

In an absorbent article such as a disposable diaper, in order to improve the fitting for the wearer, a structure containing gathers formed from elastic threads of Lycra (registered trademark) having elasticity in the waistline portion and the leg holes is adopted widely.

A process of manufacturing an absorbent article containing such gathers uses an elastic thread supply device for continuously supplying an elastic thread to a processing line in which the elastic thread is bonded on a web having a continuous nonwoven fabric, for example, (for example, Patent Literature 1). In such an elastic thread supply device, the so-called overend unwinding, in which the elastic thread is drawn sequentially in the axial core direction of a cylindrical elastic thread package around which the elastic thread is wound, is performed.

In the case of overend unwinding, because the elastic thread package does not rotate, the lead portion of a spare elastic thread package can be connected to the end portion of the elastic thread package in use. Therefore, even when one elastic thread package is used up, the processing line need not be stopped to change the elastic thread package.

On the other hand, when drawing the elastic thread by overend unwinding, a different action from that for a non-elastic thread is required. Specifically, as compared to a non-elastic thread, it is difficult to unwind an elastic thread smoothly, and the stress acting upon the elastic thread changes successively. Furthermore, a characteristic of an elastic thread is that it is stretched easily by a small amount of stress. Therefore, if an elastic thread drawn by overend unwinding is supplied as is to the processing line, then when the elastic thread is stretched in the processing line, a variation occurs in the stress acting upon the elastic thread, which might lead to a quality defect of the absorbent article.

Thus, an elastic thread supply device equipped with a tension controller to control the tension of the elastic thread drawn by overend unwinding is known (for example, Patent Literature 2). According to such an elastic thread supply device, because an elastic thread is supplied to the processing line after controlling the stress acting upon the elastic thread within a certain range by the tension controller, the quality defect of the absorbent article can be inhibited.

CITATION LIST

Patent Literature

[PTL 1] Japanese Patent Unexamined Publication No. 2005-67791 (Pages 4 and 5, FIG. 1)

[PTL 2] U.S. Patent Publication Application No. 2007/0152093 Text of Specifications

SUMMARY OF INVENTION

However, even in an elastic thread supply device equipped with the aforementioned tension controller, a variation in the stress acting upon the elastic thread after stretching still continues to occur, and further improvement was desired. Specifically, when a condition occurs where the conveyance velocity of the processing line changes suddenly, such as in the case of material patches in the processing line, the tension controller cannot follow the change in the supply velocity of the elastic thread, and a variation occurs in the stress acting upon the elastic thread.

Therefore, an object of the present invention is to provide an elastic thread supply device that can inhibit more certainly a quality defect of a product due to variation in the stress acting upon an elastic thread, when the elastic thread drawn by overend unwinding is supplied to a processing line.

An aspect of the present invention is summarized as an elastic thread supply device (an elastic thread supply device 100) configured to supply an elastic thread (an elastic thread TH) to a processing line (a processing line 30), by overend unwinding for sequential drawing of the elastic thread in an axial core direction (an axial core direction S) of a cylindrical elastic thread package (an elastic thread package P) around which the elastic thread is wound, comprising: a stress control unit (a tension controller 130) configured to control the stress acting upon the elastic thread drawn from the elastic thread package; and a drive roll (a drive roll 140) configured to supply the elastic thread dispensed from the stress control unit, to the processing line, wherein the stress control unit is configured to control the stress acting upon the elastic thread such that the stress becomes lesser than the stress acting upon the elastic thread in the processing line, and the drive roll is configured to, by operating at a supply velocity (a supply velocity v2) slower than a conveyance velocity (a conveyance velocity v1) of an article to be conveyed (a web W) that is conveyed in the processing line, supply the elastic thread to the processing line such that the elastic thread attains a percentage of stretch (a percentage of stretch m) between the drive roll and the processing line, and also, increase or decrease the supply velocity depending on a fluctuation in the conveyance velocity.

DESCRIPTION OF EMBODIMENTS

Figure 1:
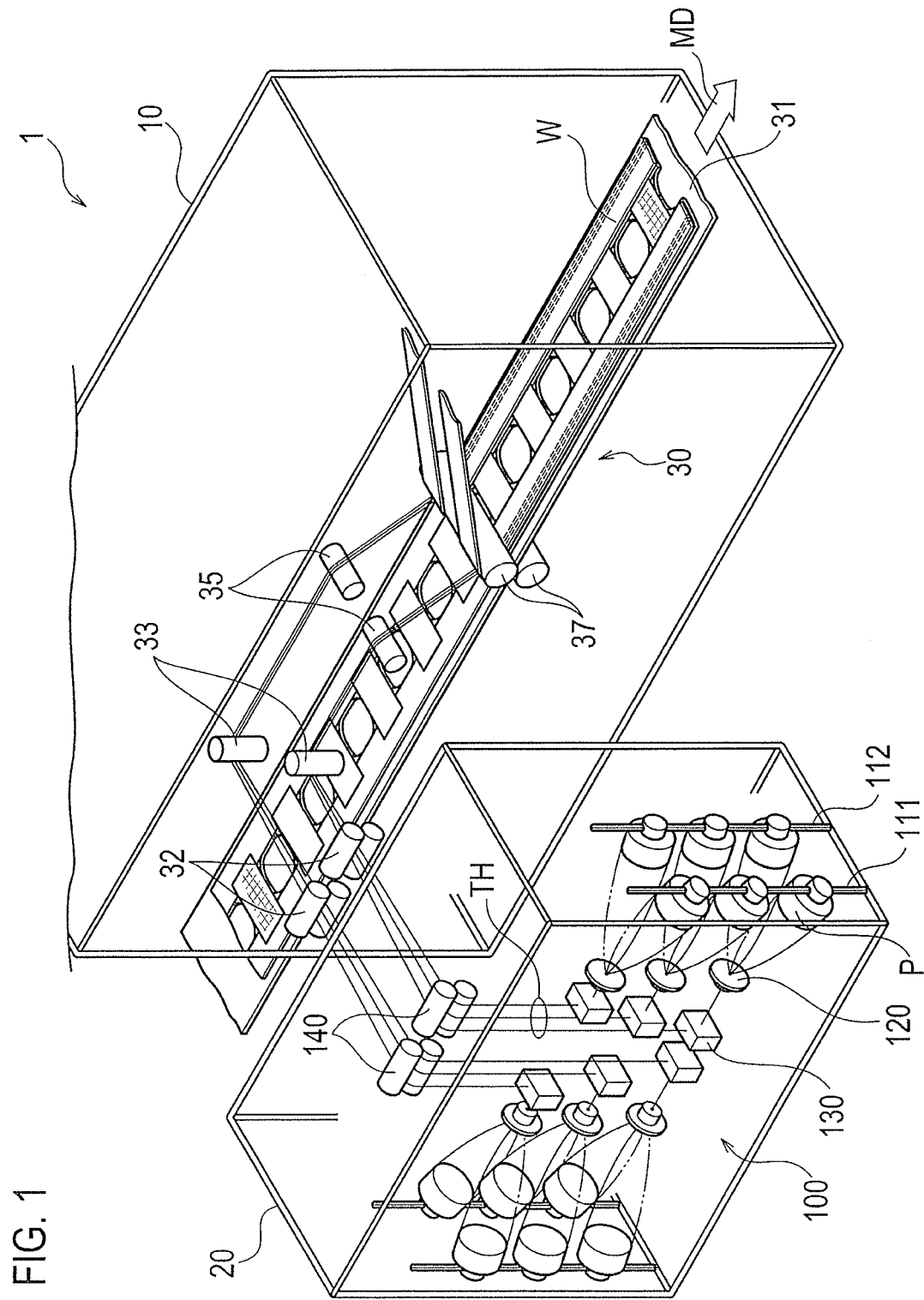
FIG. 1 is a schematic perspective view of a manufacturing device 1 according to an embodiment of the present invention.

Next, an embodiment of the elastic thread supply device according to the present invention is explained with reference to drawings. In the following description of the drawings, the same or similar reference numerals are used to designate the same or similar parts. It will be appreciated that the drawings are schematically shown and the ratio and the like of each dimension are different from the real ones.

Therefore, a specific dimension and the like should be determined in view of the following description. Moreover, among the drawings, the respective dimensional relations or ratios may differ.

Figure 2:
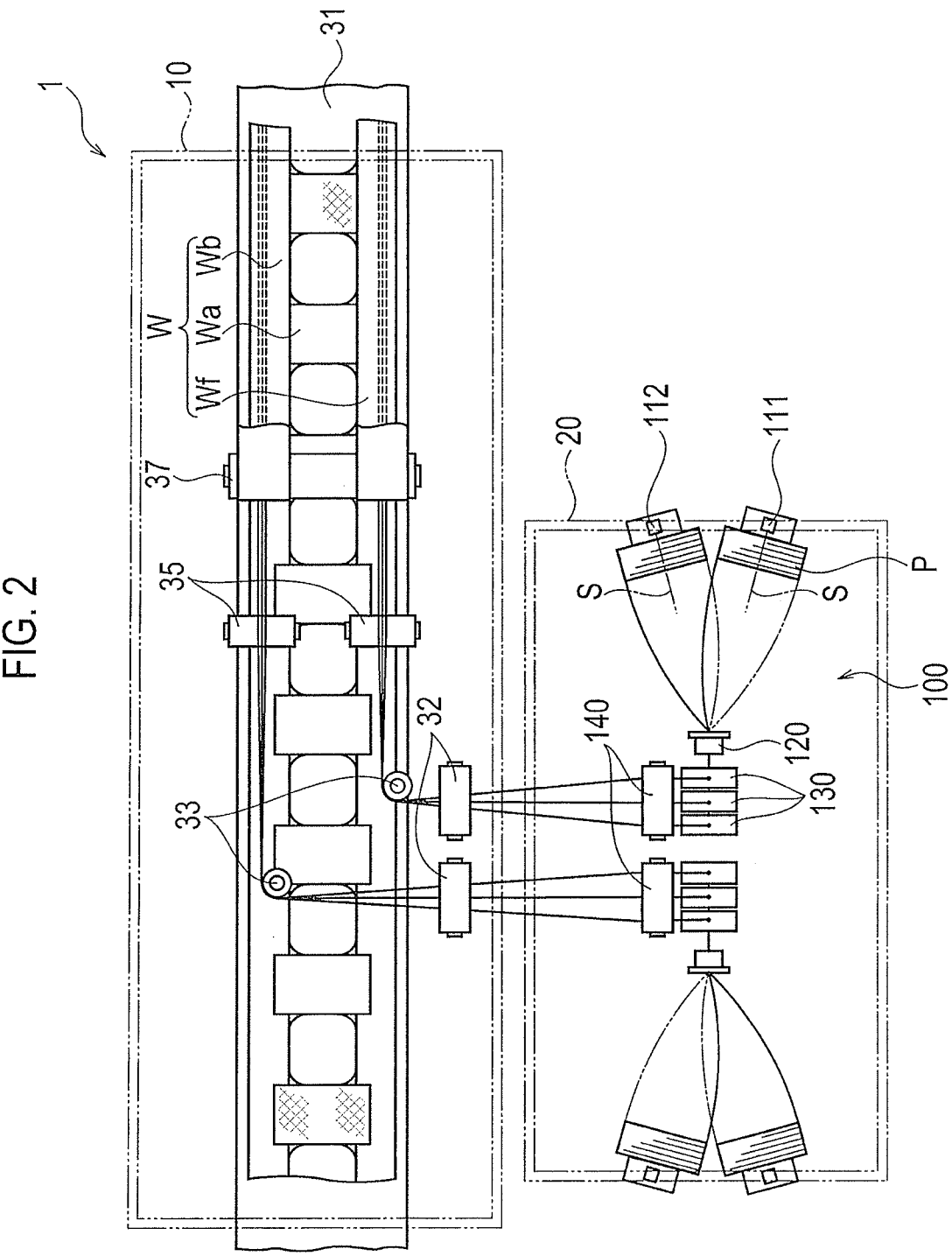
FIG. 2 is a schematic plan view of the manufacturing device 1 according to the embodiment of the present invention.

(1) Schematic Configuration of Manufacturing Device Including Elastic Thread Supply Device FIG. 1 is a schematic perspective view of a manufacturing device 1 of a disposable diaper according to the present embodiment. FIG. 2 is a schematic plan view of the manufacturing device 1 and FIG. 3 is a schematic front view of the manufacturing device 1.

Figure 3:
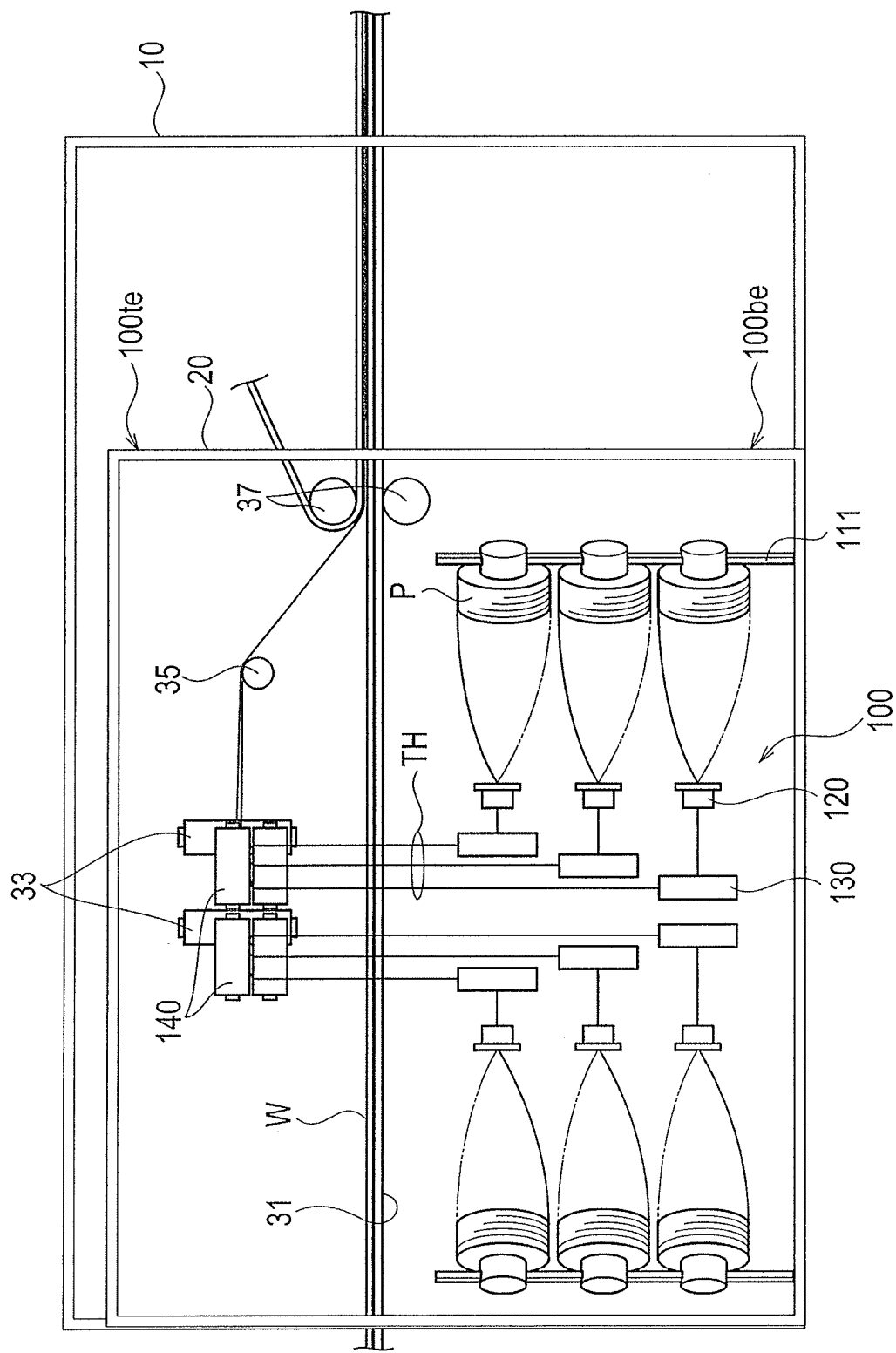
FIG. 3 is a schematic front view of the manufacturing device 1 according to the embodiment of the present invention.

As shown in FIG. 1 through FIG. 3, the manufacturing device 1 includes a line frame 10 and an unwinding frame 20. In the present embodiment, the manufacturing device 1 is used to manufacture a disposable diaper having a three-piece structure including a front body unit, an absorber, and a back body unit.

A processing line 30 is provided in the line frame 10. The processing line 30 bonds the elastic thread TH that forms the gathers of the disposable diaper on a web W having a non-woven fabric, for example, in continuation. The processing line 30 includes a conveyor 31 and a nip roll 37. Furthermore, an additional drive roll 32 and an intermediate roll 35 for dispensing the elastic thread TH at a predetermined velocity, and a free guide roll 33 for guiding the elastic thread TH are provided at the front (upstream side) of the nip roll 37.

The conveyor 31 conveys the web W (the article to be conveyed) in a machine direction MD of the manufacturing device 1. In the present embodiment, the web W is configured from a portion Wf in which the front body unit of the disposable diaper to be manufactured is in continuation, a portion Wa arranged at a predetermined interval, and a portion Wb in which the back body unit is in continuation (see FIG. 2).

The additional drive roll 32 is provided between the drive roll 140 of the elastic thread supply device 100, and the processing line 30. The additional drive roll 32 is a nip roll driven by a motor (not shown in the figure), and dispenses the elastic thread TH to the processing line 30 at a predetermined velocity. The additional drive roll 32 operates at a velocity (for example, an intermediate velocity v1') different from the supply velocity v2 of the drive roll 140 and the conveyance velocity v1.

The free guide roll 33 guides the elastic thread TH supplied from the elastic thread supply device 100 provided on the unwinding frame 20, to the processing line 30. Specifically, the free guide roll 33 turns over the supply direction of the elastic thread TH supplied via the additional drive roll 32 from a direction perpendicular to the machine direction MD in which the web W is conveyed, by 90 degrees in a plan view of the elastic thread supply device 100. In the present embodiment, the free guide roll 33 is provided between the additional drive roll 32 and the intermediate roll 35. The free guide roll 33 is a rotatable roll that does not have a drive source such as a motor; and rotates as a result of the contact and movement of the elastic thread TH.

The intermediate roll 35 is provided between the free guide roll 33 and the nip roll 37. The elastic thread TH supplied from the elastic thread supply device 100 provided on the unwinding frame 20 is relayed to the nip roll 37. The intermediate roll 35 is driven by a motor (not shown in the figure), and dispenses the elastic thread TH to the processing line 30 at a predetermined velocity.

The intermediate roll 35 operates at the same velocity as the additional drive roll 32. The intermediate roll 35 can also function as a free roll that is not driven by a motor. Furthermore, the intermediate roll 35 may also have the function of adjusting the pitch of a pair of elastic threads TH.

The nip roll 37 bonds the elastic thread TH supplied via the additional drive roll 32, the free guide roll 33, and the intermediate roll 35 at a predetermined position on the web W. Specifically, the nip roll 37 is driven by a motor (not shown in the figure), and presses the web W conveyed by the conveyor 31 and the elastic thread TH in a sandwiched state. When the web W and the elastic thread TH are pressed by the nip roll 37, the elastic thread TH is affixed at a predetermined position of the web W where an adhesive has been applied.

The web W conveyed by the conveyor 31 is conveyed in the machine direction MD at the conveyance velocity v1. Similarly, the nip roll 37 is driven at the conveyance velocity v1.

The elastic thread supply device 100 is provided on the unwinding frame 20. The elastic thread supply device 100 includes a plate-shaped guide 120, a tension controller 130, and a drive roll 140. Furthermore, a plurality of elastic thread packages P are fitted on the unwinding frame 20. The elastic thread packages P are supported by a support bar 111 or a support bar 112.

The elastic thread supply device 100 sequentially draws the elastic thread TH from an elastic thread package P, and supplies the drawn elastic thread TH to the processing line 30. FIG. 1 through FIG. 3 are schematic drawings, and the elastic thread packages P fitted on the unwinding frame 20 are not limited to the number shown in FIG. 1 through FIG. 3.

(2) Configuration of the Elastic Thread Supply Device

Next, a specific configuration of the elastic thread supply device 100 is explained. In the elastic thread supply device 100, overend unwinding, in which the elastic thread TH is drawn sequentially in the axial core direction S (see FIG. 2) of a cylindrical elastic thread package P around which the elastic thread TH is wound, is performed.

During overend unwinding, the lead portion of the spare elastic thread package P can be connected to the end portion (so-called hind thread) of the elastic thread package P that is in use. For example, the end portion of the elastic thread package P supported by the support bar 111 and positioned at the topmost level can be connected to the lead portion of the elastic thread package P supported by the support bar 112 and positioned similarly at the topmost level.

Note that a known method, such as thermal fusion bonding can be used for connecting the elastic thread TH of the elastic thread package P that is in use to the elastic thread TH of the spare elastic thread package P. Furthermore, any one of a polyether series, a polyester series, or a polyurethane elastic thread made from a polyether and polyester series can be used as the elastic thread TH as long as the fineness of the thread is such that can be used in a disposable diaper, which is generally between 270 and 1200 dtex.

As described above, the elastic thread supply device 100 includes a plurality of plate-shaped guides 120, tension controllers 130, and drive rolls 140. In the present embodiment, the plate-shaped guides 120, the tension controllers 130, and the drive rolls 140 are loaded together with the elastic thread package P on the unwinding frame 20 separate from the line frame 10 on which the processing line 30 is loaded. In FIG. 1 through FIG. 3, only the plate-shaped guide 120, the tension controller 130, and the drive roll 140 arranged on the right side have been marked, but on the left side, the plate-shaped guide 120, the tension controller 130, and the drive roll 140 are arranged in symmetry with the right side.

The plate-shaped guide 120 is a guide in the shape of a plate that guides the elastic thread TH drawn from the elastic thread package P towards the tension controller 130. A through hole (not shown in the figure) through which the elastic thread TH passes while sliding is formed in the plate-shaped guide 120.

The tension controller 130 constitutes a stress control unit configured to control the stress acting upon the elastic thread TH drawn from the elastic thread package P via the plate-shaped guide 120. In the present embodiment, a device using a servo motor and a tension sensor, as described in Patent Literature 2, is used. The device that can be used as the tension controller 130 is not limited to the device described in Patent Literature 2.

In the present embodiment, the tension controller 130 is configured to control the stress acting upon the elastic thread TH such that the stress becomes lesser than the stress acting upon the elastic thread TH in the processing line 30. Specifically, the tension controller 130 is configured to set the stress acting upon the elastic thread TH between 10 and 15 cN. Specifically, the tension controller 130 is configured to set the stress acting upon the dispensed elastic thread TH to a constant value in the range of 10 to 15 cN (for example, 12 cN).

As a result, the stress acting upon the elastic thread TH is controlled within a constant range, and the amount of the elastic thread TH drawn from the elastic thread package P per unit time is controlled. Specifically, the stress acting upon the elastic thread TH is controlled such that the percentage of stretch m' of the elastic thread TH drawn from the tension controller 130 becomes around 1.1 to 1.3 times.

The drive roll 140 is configured to dispense the elastic thread TH from the tension controller 130, and at the same time, supply the dispensed elastic thread TH to the processing line 30. Furthermore, FIG. 4 is an enlarged perspective view of the drive roll 140.

Figure 4:
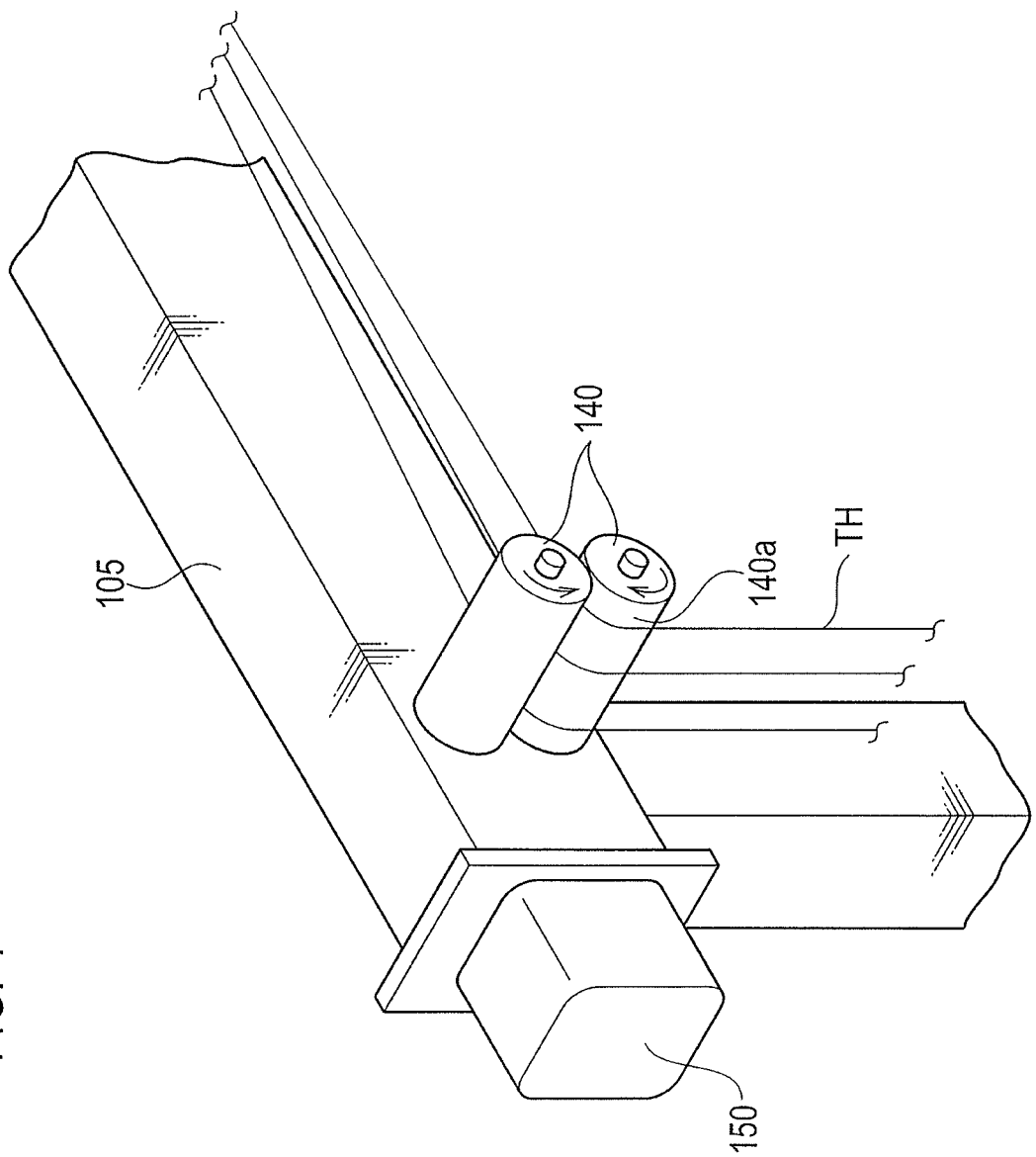
FIG. 4 is an enlarged perspective view of a drive roll 140 according to the embodiment of the present invention.

As shown in FIG. 4, the drive roll 140 is driven by the servo motor 150. The drive roll 140 and the servo motor 150 are mounted on a rail 105 constituting the unwinding frame 20. When the drive roll 140 is rotated by the servo motor 150 in the direction of the arrow shown in FIG. 4 at a supply velocity v2, the elastic thread TH is dispensed towards the processing line 30.

Here, in the present embodiment, the supply velocity v2 is slower than the conveyance velocity v1 of the web W conveyed in the processing line 30. That is, because the drive roll 140 operates at a supply velocity v2 slower than the conveyance velocity v1, the drive roll 140 supplies the elastic thread TH to the processing line 30 such that the elastic thread TH attains the percentage of stretch m (for example, two times) between the drive roll 140 and the processing line 30.

Furthermore, depending on the fluctuation in the conveyance velocity v1 of the processing line 30, the servo motor 150 increases or decreases the supply velocity v2 of the drive roll 140. Specifically, the servo motor 150 can acquire the feedback information of the conveyance velocity v1 output from the processing line 30. Based on the acquired feedback information, the servo motor 150 increases or decreases the supply velocity v2. The provision of the feedback information of the conveyance velocity v1 to the servo motor 150 is realized through an electrical connection between a sensor (not shown in the figure) configured to detect the conveyance velocity v1 in the processing line 30 and the servo motor 150, for example.

In the present embodiment, absolutely no guide rolls are used on the unwinding frame 20 between the tension controller 130 and the drive roll 140 to guide the elastic thread TH in a predetermined direction, and the elastic thread TH dispensed from the tension controller 130 is transferred directly to the drive roll 140. That is, in order to directly transfer the elastic thread TH dispensed from the tension controller 130 to the drive roll 140, the unwinding frame 20 supports the drive roll 140 almost directly above the tension controller 130. Furthermore, on the unwinding frame 20, the drive roll 140 is supported so as to supply the elastic thread TH from a top end 100te of the unwinding frame 20 to the line frame 10 (processing line 30). Therefore, the movement direction of the elastic thread TH is changed by almost 90 degrees in the drive roll 140. The drive roll 140 is desired to be positioned at 2 m or more from the loading surface of the unwinding frame 20.

(3) Operation of Supplying Elastic Thread

Figure 5:
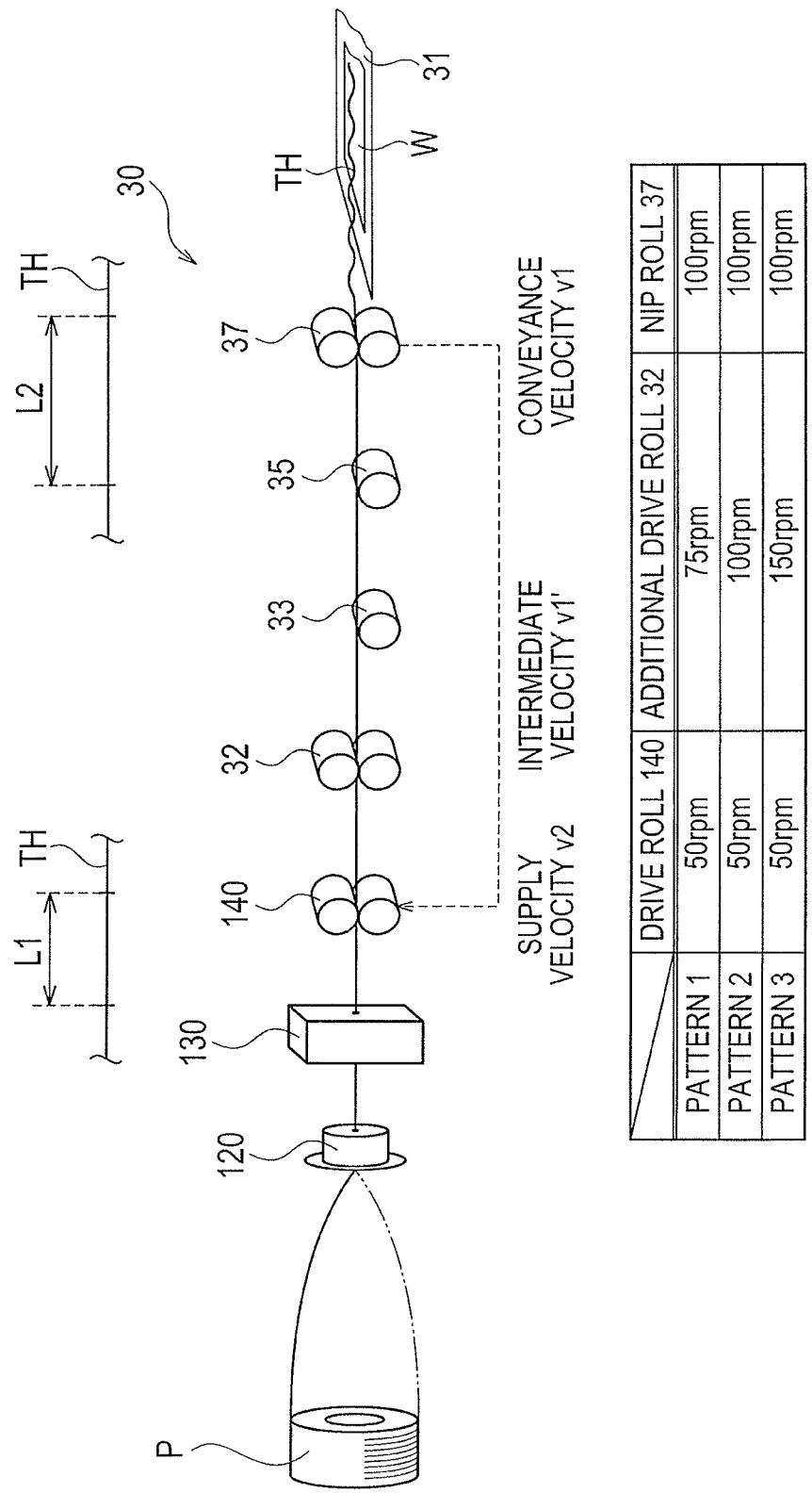
FIG. 5 is an explanatory drawing of an operation of supplying an elastic thread TH, by the manufacturing device 1, to a processing line 30 according to the embodiment of the present invention.

FIG. 5 is an explanatory drawing of an operation of supplying the elastic thread TH, by the aforementioned manufacturing device 1, to the processing line 30. As shown in FIG. 5, the elastic thread TH drawn from the elastic thread package P through overend unwinding passes through the tension controller 130 via the plate-shaped guide 120.

Almost no stress is acting upon the elastic thread TH at a position immediately before the elastic thread TH enters the tension controller 130. Therefore, the percentage of stretch m of the elastic thread TH is also approximately one time. The percentage of stretch is the ratio of the length L1 of the elastic thread TH before stretching to the length L2 (L2/L1) of the elastic thread after stretching.

As described above, the tension controller 130 is configured to set the stress acting upon the elastic thread TH to a constant value in the range of 10 to 15 cN (for example, 12 cN). Therefore, the stress acting upon the elastic thread TH dispensed from the tension controller 130 is still less. Specifically, the percentage of stretch m' of the elastic thread TH dispensed from the tension controller 130 is approximately 1.1 to 1.3 times. Although the tension controller 130 and the processing line 30 (nip roll 37) are not interlocked, if the conveyance velocity v1 changes, the supply velocity v2 of the elastic thread TH also changes, as described later. Therefore, the velocity at which the elastic thread TH is dispensed from the tension controller 130 may also change, but the stress acting upon the elastic thread TH still remains less.

The drive roll 140 operates at a supply velocity v2, as described above. The supply velocity v2 is set slower than the conveyance velocity v1 of the web W conveyed in the processing line 30. For example, the drive roll 140 operates at a supply velocity v2 of 50 rpm.

Furthermore, depending on the fluctuation in the conveyance velocity v1, the drive roll 140 is configured to increase or decrease the supply velocity v2. That is, the drive roll 140 and the processing line 30 (nip roll 37) are interlocked. Specifically, based on the feedback information of the conveyance velocity v1 from the processing line 30, the drive roll 140 is configured to control the supply velocity v2 so as to satisfy the relationship of (expression 1), and to supply the elastic thread TH to the processing line 30.

Supply velocity $v2$=Conveyance velocity $v1$/percentage of stretch $m$     (expression 1)

Note that the percentage of stretch m of (expression 1) is a value between the drive roll 140 and the nip roll 37. The elastic thread TH supplied from the drive roll 140 reaches the additional drive roll 32. The additional drive roll 32 can operate at an intermediate velocity v1' (for example, pattern 1 shown in FIG. 5) different from the supply velocity v2 of the drive roll 140 and the conveyance velocity v1. Specifically, the additional drive roll 32 can operate at a velocity (for example, 75 rpm) that is higher than the supply velocity v2 of the drive roll 140, and lower than the conveyance velocity v1.

The elastic thread TH dispensed from the additional drive roll 32 reaches the intermediate roll 35 via the free guide roll 33. The intermediate roll 35 operates at the same velocity as the additional drive roll 32. The elastic thread TH reaches the nip roll 37 via the intermediate roll 35, and is bonded on the web W. The nip roll 37 operates at a conveyance velocity v1 together with the conveyor 31.

Thus, when the elastic thread TH that is stretched at the stipulated percentage (for example, two times) is bonded on the web W, the stress that is necessary for a disposable diaper is applied to the elastic thread TH.

According to the manufacturing device 1 including the aforementioned elastic thread supply device 100. The drive roll 140 is provided between the tension controller 130 and the processing line 30. The drive roll 140 operates at a supply velocity v2 that is slower than the conveyance velocity v1 of the web W. Therefore, the velocity of the elastic thread TH dispensed from the tension controller 130 can be suppressed, and the stress acting upon the elastic thread TH can be reduced. That is, the magnification of the elastic thread TH in the tension controller 130 can be reduced.

Figure 6:
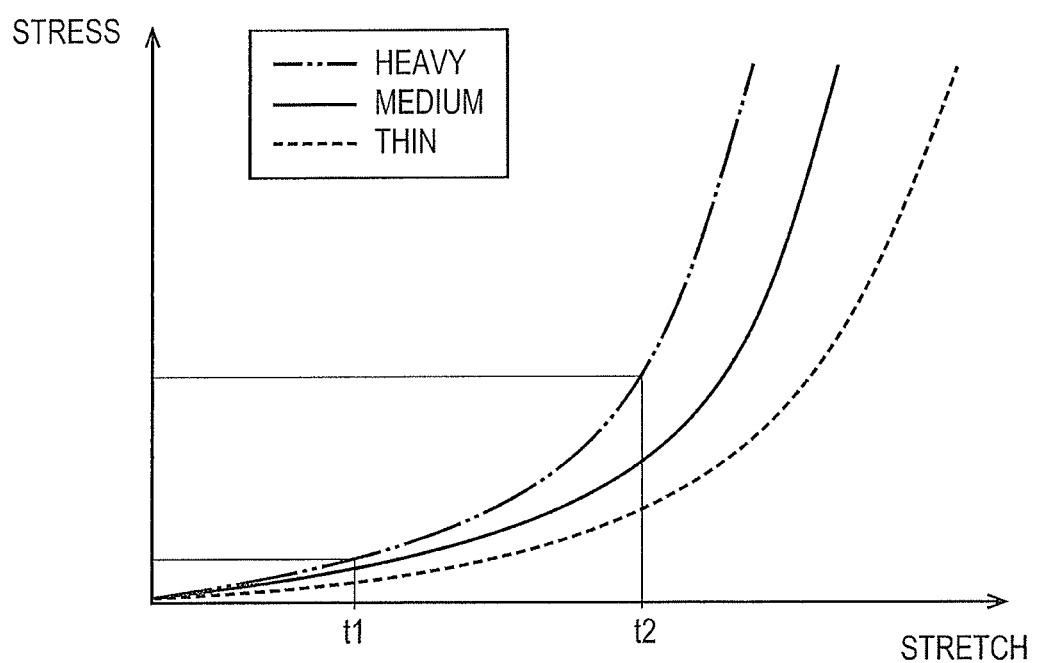
FIG. 6 is a graph that schematically illustrates the relationship between the stress acting upon the elastic thread TH and the percentage of stretch.

Here, FIG. 6 is a graph that schematically illustrates the relationship between the stress acting upon elastic threads TH having different fineness, and the percentage of stretch. As shown in FIG. 6, due to the difference in the fineness (thickness) of the elastic thread TH, the relationship between the stress acting upon the elastic thread TH and the stretch varies. That is, from the viewpoint of preventing a variation in the stress acting upon the elastic thread TH in the product (disposable diaper) stage, it is desired to dispense the elastic thread TH from the tension controller 130 in a state when the smallest possible stress is acting upon the elastic thread TH (for example, the t1 position) rather than the state when a high stress is acting upon the elastic thread TH (for example, the t2 position). For example, when the velocity of the dispensed elastic thread TH (rotation speed of the drive roll 140) changes even slightly (or when the rotation velocity of the drive roll 140 changes even slightly (changes by the same stress)), the amount of change in the stress acting upon the elastic thread TH becomes lesser at the t1 position than the t2 position. Therefore, the variation in the stress acting upon the elastic thread TH is prevented.

If an attempt is made to control the stress acting upon the elastic thread TH by only the drive roll 140 and the additional drive roll 32, without using the tension controller 130, the amount of supply of the elastic thread TH, when the elastic thread TH is drawn from the elastic thread package P, varies due to the expansion and contraction of the elastic thread TH. Therefore, the percentage of stretch m of the elastic thread TH is not constant, and the stress applied to the elastic thread TH within the disposable diaper varies.

Furthermore, the drive roll 140 operates at a supply velocity v2 that is slower than the conveyance velocity v1 of the web W. Therefore, even when the conveyance velocity v1 changes, the amount (weight) of the elastic thread TH supplied to the processing line 30 per unit time can be controlled within a constant range. As a result, even when the conveyance velocity v1 changes, the stress necessary for a disposable diaper is easy to apply to the elastic thread TH.

That is, according to the elastic thread supply device 100, when the elastic thread TH drawn by overend unwinding is supplied to the processing line 30, the quality defect of the disposable diaper occurring due to the variation in the stress acting upon the elastic thread TH can be inhibited.

In the present embodiment, an additional drive roll 32 operating at an intermediate velocity v1' that is higher than the supply velocity v2 and lower than the conveyance velocity v1 is provided. Therefore, since the stress acting upon the elastic thread TH increases gradually, it becomes easy to more precisely and certainly apply the desired stress to the elastic thread TH.

In the present embodiment, the tension controller 130 and the drive roll 140 are loaded along with the elastic thread package P on the unwinding frame 20 separate from the line frame 10. Therefore, even when the number of the elastic threads TH being handled increases, the expansion of the elastic thread package P, the tension controller 130, and the drive roll 140 is easy. Furthermore, when the interval between the elastic threads TH upon which a low stress is acting becomes longer, the elastic threads TH get deformed easily under the empty weight of the elastic threads TH, which makes it necessary to support the elastic threads TH with a free roll. However, the interposition of such a free roll is not desired as it leads to a variation in the stress acting upon the elastic thread TH. According to the present embodiment, such a problem can also be evaded because the elastic thread package P, the tension controller 130, and the drive roll 140 are in close proximity.

In the present embodiment, the elastic thread TH is supplied from the top end 100te of the unwinding frame 20 to the line frame 10 (processing line 30). Therefore, even when the elastic thread package P, the tension controller 130, and the drive roll 140 are arranged away from the line frame 10, the elastic thread TH transferred from the unwinding frame 20 to the line frame 10 does not obstruct the passage of the operator.

(4) Other Embodiments

So far, the present invention is disclosed through the above embodiments. However, it should not be interpreted that the statements and drawings constituting a part of the present disclosure limit the present invention. From this disclosure, a variety of alternate embodiments, examples, and applicable techniques will become apparent to one skilled in the art.

For example, the embodiments of the present invention may be altered in the following ways. In the aforementioned embodiment, an example in which the elastic thread TH is supplied to the processing line 30 according to pattern 1 shown in FIG. 5 has been explained, however, the drive roll 140, the additional drive roll 32, and the nip roll 37 may follow pattern 2 and pattern 3 as well. That is, the additional drive roll 32 and the nip roll 37 may operate at the same velocity, or the additional drive roll 32 may operate at a velocity faster than the conveyance velocity v1.

When the additional drive roll 32 operates at a velocity faster than the conveyance velocity v1 (see pattern 3 in FIG. 5), the elastic thread TH that has been stretched once between the drive roll 140 and the additional drive roll 32 gets contracted between the additional drive roll 32 and the nip roll 37, and therefore, the stress applied to the elastic thread TH is stabilized.

Additionally, the additional drive roll 32 and the intermediate roll 35 may be substituted by a free roll, or may not necessarily be provided. Furthermore, a traverse mechanism for swinging the elastic thread TH in the machine direction MD may be provided in place of the free guide roll 33 and the intermediate roll 35.

In the aforementioned embodiment, the elastic thread TH was supplied from the top end 100te of the unwinding frame 20 to the line frame 10, however, the elastic thread TH may be supplied from a bottom end 100be of the unwinding frame 20 to the line frame 10. Furthermore, the tension controller 130 and the drive roll 140 need not necessarily be loaded on the unwinding frame 20. If possible, the tension controller 130 and the drive roll 140 may be loaded on the line frame 10.

In the aforementioned embodiment, a disposable diaper has been explained as an example, however, the applicability of the present invention is not limited thereto, and the article to be conveyed by the conveyor 31 need not necessarily be a continuous body like the web W. For example, a semi-finished sanitary napkin containing gathers may be conveyed at a predetermined interval.

As described above, needless to say, the present invention includes various embodiments and the like not described here. Therefore, the technical range of the present invention is to be defined only by the inventive specific matter according to the adequate claims from the above description.

As described above, needless to say, the present invention includes various embodiments and the like not described here. Therefore, the technical range of the present invention is to be defined only by the inventive specific matter according to the adequate claims from the above description.

The entire contents of Japanese Patent Application Laid-open No. 2009-298639 (filed on Dec. 28, 2009) are incorporated in the present specification by reference.

INDUSTRIAL APPLICABILITY

According to the present invention, it is possible to provide an elastic thread supply device that can inhibit more certainly a quality defect of a product due to variation in the stress acting upon an elastic thread, when the elastic thread drawn by overend unwinding is supplied to a processing line.

REFERENCE SIGNS LIST

1 . . . Manufacturing device, 10 . . . Line frame, 20 . . . Unwinding frame, 30 . . . Processing line, 31 . . . Conveyor, 32 . . . Additional drive roll, 33 . . . Free guide roll, 35 . . . Intermediate roll, 37 . . . Nip roll, 100 . . . Elastic thread supply device, 100be . . . Bottom end, 100te . . . Top end, 105 . . . Rail, 111, 112 . . . Support bar, 120 . . . Plate-shaped guide, 130 . . . Tension controller, 140 . . . Drive roll, 140a . . . Groove, 150 . . . Servo motor, MD . . . Machine direction, P . . . Elastic thread package, S . . . Axial core direction, TH . . . Elastic thread, W . . . Web

The invention claimed is:

1. An elastic thread supply device configured to supply an elastic thread to a processing line, by overend unwinding for sequential drawing of the elastic thread in an axial core direction of a cylindrical elastic thread package around which the elastic thread is wound, comprising:
   a stress control unit configured to control the stress acting upon the elastic thread drawn from the elastic thread package; and
   a drive roll configured to supply the elastic thread dispensed from the stress control unit, to the processing line, wherein
   the stress control unit is configured to control the stress acting upon the elastic thread such that the stress becomes lesser than the stress acting upon the elastic thread in the processing line, and
   the drive roll is configured to, by operating at a supply velocity slower than a conveyance velocity of an article to be conveyed that is conveyed in the processing line, supply the elastic thread to the processing line such that the elastic thread attains a predetermined percentage of stretch between the drive roll and the processing line, and also, increase or decrease the supply velocity depending on a fluctuation in the conveyance velocity;
   wherein the drive roll is arranged downstream of the stress control unit, between the stress control unit and the processing line.

2. The elastic thread supply device according to claim 1, wherein
   the stress control unit is configured to set the stress acting upon the elastic thread between 10 and 15 cN.

3. The elastic thread supply device according to claim 1, further comprising:
   an additional drive roll provided between the drive roll and the processing line, and configured to operate at a velocity different from the supply velocity of the drive roll and the conveyance velocity.

4. The elastic thread supply device according to claim 3, wherein
   the additional drive roll is configured to operate at a velocity higher than the supply velocity of the drive roll, and lower than the conveyance velocity.

5. The elastic thread supply device according to claim 3, wherein
   the additional drive roll is configured to operate at a velocity higher than the conveyance velocity.

6. The elastic thread supply device according to claim 1, wherein
   the stress control unit and the drive roll are loaded along with the elastic thread package on an unwinding frame separate from a line frame on which the processing line is loaded.

7. The elastic thread supply device according to claim 6, wherein
   the unwinding frame is configured to, without using a guide roll to guide the elastic thread in a predetermined direction, support the stress control unit and the drive roll such that the elastic thread dispensed from the stress control unit is transferred directly to the drive roll.

8. The elastic thread supply device according to claim 6, wherein
   the unwinding frame is configured to support the drive roll so as to supply the elastic thread to the line frame from a top end or a bottom end of the unwinding frame.

9. The elastic thread supply device according to claim 1, wherein
   the drive roll is configured to, by increasing or decreasing the supply velocity depending on a fluctuation in the conveyance velocity, control the predetermined percentage of stretch of the elastic thread between the drive roll and the processing line.

10. An elastic thread supply device configured to supply an elastic thread to a processing line, by overend unwinding for sequential drawing of the elastic thread in an axial core direction of a cylindrical elastic thread package around which the elastic thread is wound, comprising:
   a stress control unit configured to control the stress acting upon the elastic thread drawn from the elastic thread package; and a drive roll configured to supply the elastic thread dispensed from the stress control unit, to the processing line, wherein the stress control unit is configured to control the stress acting upon the elastic thread such that the stress becomes lesser than the stress acting upon the elastic thread in the processing line, and the drive roll is configured to, by operating at a supply velocity slower than a conveyance velocity of an article to be conveyed that is conveyed in the processing line, supply the elastic thread to the processing line such that the elastic thread attains a percentage of stretch between the drive roll and the processing line, and also, increase or decrease the supply velocity depending on a fluctuation in the conveyance velocity, the elastic thread supply device further comprising:

an additional drive roll provided between the drive roll and the processing line, and configured to operate at a velocity different from the supply velocity of the drive roll and the conveyance velocity, wherein the additional drive roll is configured to operate at a velocity higher than the supply velocity of the drive roll, and lower than the conveyance velocity.

11. An elastic thread supply device configured to supply an elastic thread to a processing line, by overend unwinding for sequential drawing of the elastic thread in an axial core direction of a cylindrical elastic thread package around which the elastic thread is wound, comprising:

a stress control unit configured to control the stress acting upon the elastic thread drawn from the elastic thread package; and a drive roll configured to supply the elastic thread dispensed from the stress control unit, to the processing line, wherein the stress control unit is configured to control the stress acting upon the elastic thread such that the stress becomes lesser than the stress acting upon the elastic thread in the processing line, and the drive roll is configured to, by operating at a supply velocity slower than a conveyance velocity of an article to be conveyed that is conveyed in the processing line, supply the elastic thread to the processing line such that the elastic thread attains a percentage of stretch between the drive roll and the processing line, and also, increase or decrease the supply velocity depending on a fluctuation in the conveyance velocity, the elastic thread supply device further comprising:

an additional drive roll provided between the drive roll and the processing line, and configured to operate at a velocity different from the supply velocity of the drive roll and the conveyance velocity, wherein the additional drive roll is configured to operate at a velocity higher than the conveyance velocity.

* * * * *